US00PP34706P2

(12) United States Plant Patent
Ruter

(10) Patent No.: US PP34,706 P2
(45) Date of Patent: Nov. 1, 2022

(54) ***HIBISCUS* PLANT NAMED 'RUTHIB5'**

(50) Latin Name: *Hibiscus*
Varietal Denomination: RutHib5

(71) Applicant: University of Georgia Research Foundation, Inc., Athens, GA (US)

(72) Inventor: John M. Ruter, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 6 days.

(21) Appl. No.: 17/378,341

(22) Filed: Jul. 16, 2021

(51) Int. Cl.
*A01H 5/02* (2018.01)
*A01H 6/60* (2018.01)

(52) U.S. Cl.
USPC ..... Plt./257
CPC ..... *A01H 6/608* (2018.05)

(58) Field of Classification Search
USPC ..... Plt./257
CPC ..... A01H 6/608; A01H 5/02
See application file for complete search history.

*Primary Examiner* — Keith O. Robinson
(74) *Attorney, Agent, or Firm* — Thomas Horstemeyer, LLP

(57) ABSTRACT

A new and distinct cultivar of *Hibiscus* plant named 'RutHib5' is characterized by a combination of compact rounded form with medium vigor, attractive white flowers with a red eye, bicolor, reddish green foliage with pubescence, and good resistance to Alternaria alternata, Cercospora, and *Hibiscus* sawfly.

5 Drawing Sheets

Botanical designation: *Hibiscus*.
Cultivar denomination 'RutHib5'.

BACKGROUND OF THE INVENTION

The present invention relates to a new and distinct cultivar of *Hibiscus*, botanically know as *Hibiscus*, and hereinafter referred to by the cultivar name 'RutHib5'.

The new *Hibiscus* 'RutHib5' is a product of a planned breeding program conducted by the inventors at a horticulture farm in Watkinsville, Ga. The objective of the *Hibiscus* breeding is to create new plant cultivars with ornamental leaf distinctions, abundant flowers, and tolerance to insects and pathogens. These and other qualities are enumerated herein.

The new *Hibiscus* 'RutHib5' is a product of a 2016 cross of *Hibiscus moscheutos* 'RutHib2' (U.S. Plant Pat. No. 30,853) x *Hibiscus grandiflorus* (unpatented), the progeny of which (named Hib2015-76) was then backcrossed with the parent *Hibiscus moscheutos* 'RutHib2' to produce the new 'RutHib5.' The seedling 'RutHib5' was selected in 2017 and has been evaluated through trials at a horticulture farm in Watkinsville, Ga. and West Grove, Pa.

The original plant is still growing at the horticultural farm in Georgia, and asexual reproduction of the new *Hibiscus* 'RutHib5' using vegetative terminal cuttings in controlled environment has been continued in West Grove, Pa. since 2017. Observations of the resulting 'RutHib5' progeny have shown that the unique features of this new *Hibiscus* 'RutHib5' are stable and reproduced true to type in successive generations.

SUMMARY OF THE INVENTION

The new *Hibiscus* cultivar 'RutHib5' has not been observed under all possible environmental conditions. The phenotype may vary somewhat with variations in environment and cultural practices such as temperature, water and fertility levels, soil types, and light intensity without, however, any variance in genotype.

The following traits have been repeatedly observed and are determined to be the unique and distinguishing characteristics of the new *Hibiscus* cultivar named 'RutHib5'. In combination, these traits set 'RutHib5' apart from all other existing varieties of *Hibiscus* known to the inventors.

1. compact rounded form with medium vigor;
2. attractive white flowers with a red eyespot and veins (*H. grandiflorus* has no eyespot);
3. bicolor, reddish green foliage with pubescence;
4. good resistance to Alternaria alternata, Cercospora, and intermediate resistance to *Hibiscus* sawfly (*Atomacera depcepta*), which is lacking in *H. moscheutos* 'Summer Storm'.

Specifically, plants of the new *Hibiscus* differ from the closest related cultivars, including the unpatented female parent *H. moscheutos* Hib2015-76, the male parent *H. moscheutos* 'RutHib2', and the grandparent *Hibiscus grandiflorus* in at least the following characteristics:

TABLE 1

| | Height × width (cm) | Abaxial pubescence | Petiole and vein color |
|---|---|---|---|
| 'RutHib2'* | 75 × 110 | none | Red |
| *H. grandiflorus* | 130 × 150 | dense | Green |
| 'RutHib5'* | 90 × 110 | moderate | Red |
| *H. moscheutos* 'Summer Storm' | 105 × 130 | none | Red |

Data: May 26, 2021 Watkinsville, GA. Flowering Jun. 26, 2021*

BRIEF DESCRIPTION OF THE PHOTOGRAPHS

The accompanying colored photographic illustrations show the overall appearance and distinct characteristics of the new cultivar of *Hibiscus* 'RutHib5' showing the colors as true as possible. Colors in the photographs may differ slightly from the color values cited in the detailed botanical description, which accurately describes the colors of the new *Hibiscus* 'RutHib5'. The photographs were taken of plants grown outdoors in West Grove, Pa. around August 2020.

The photographs labeled FIG. 1A and FIG. 1B depict close up views of a typical flower of the new *Hibiscus* 'RutHib5' plant in different lighting, showing the large white blooms, vibrant reddish-deep pink eyespots, and green foliage.

The photograph labeled FIG. 2 depicts a more distant view of a typical 3-year-old summer 'RutHib5' plant growing alongside other *Hibiscus* plants of different form and color, illustrating the large, white flowers of the 'RutHib5' cultivar with deep reddish-pink eyespots and generally compact form.

DETAILED BOTANICAL DESCRIPTION

Figure 1A:
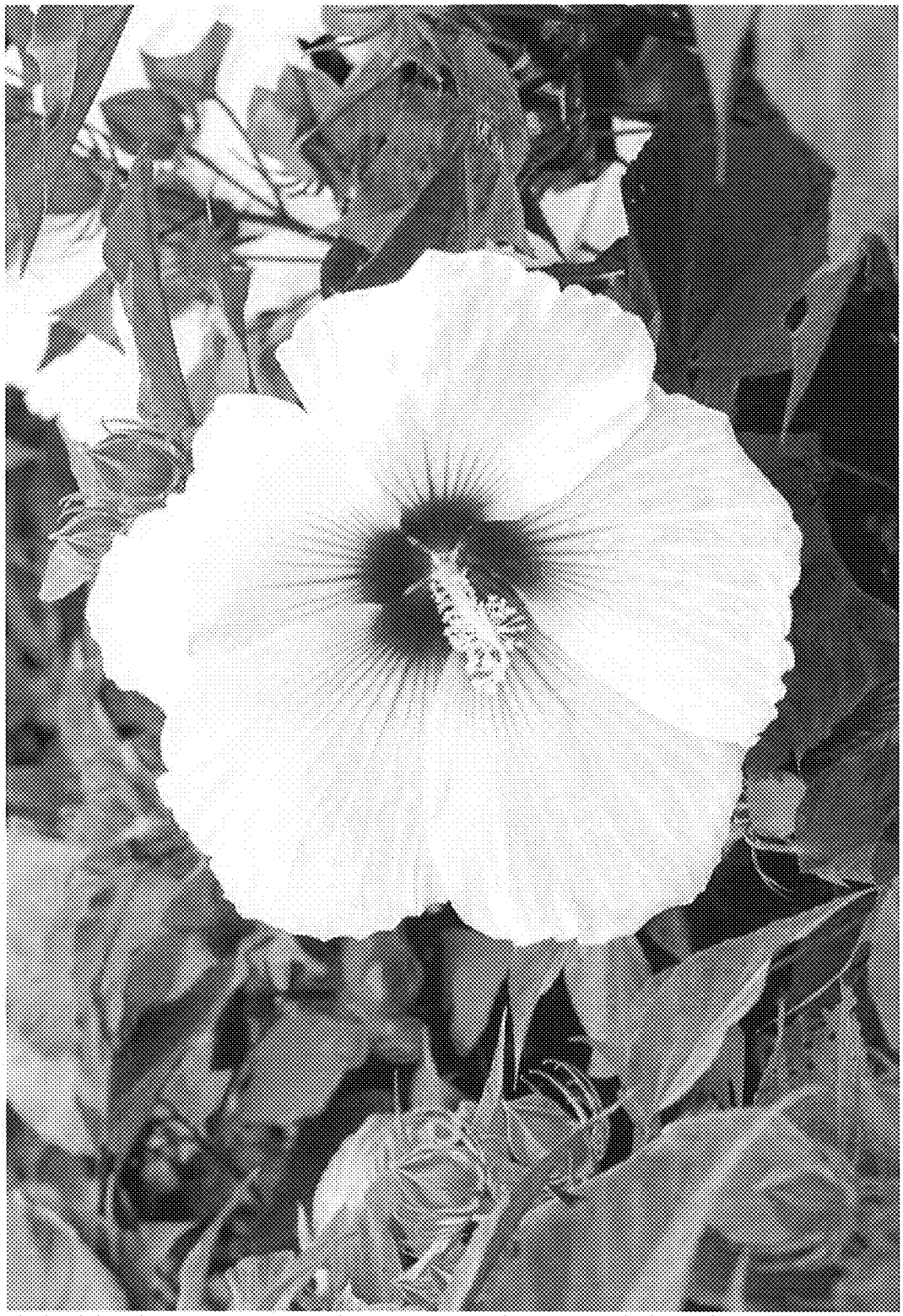
Figure 1B:
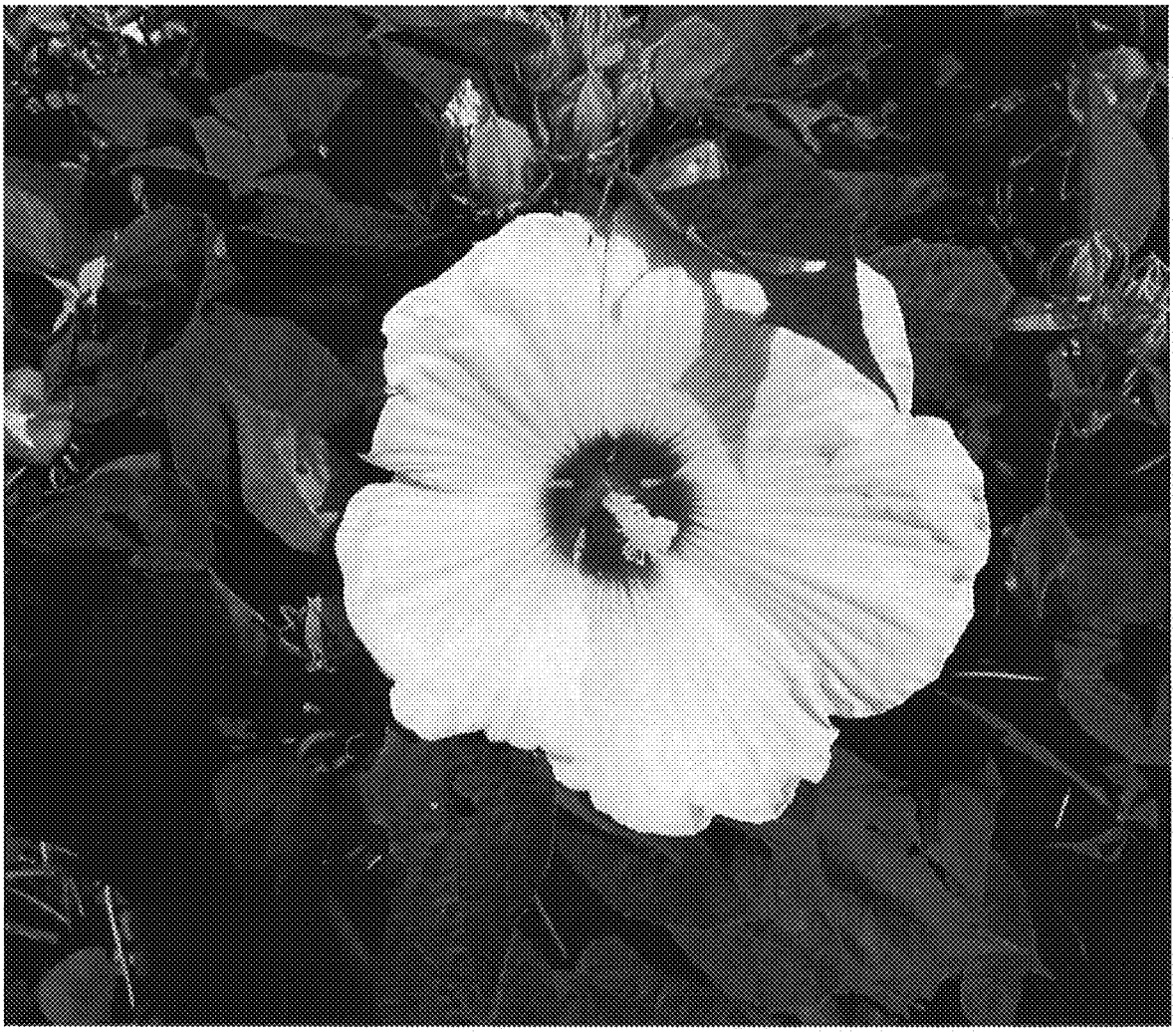
Figure 2:
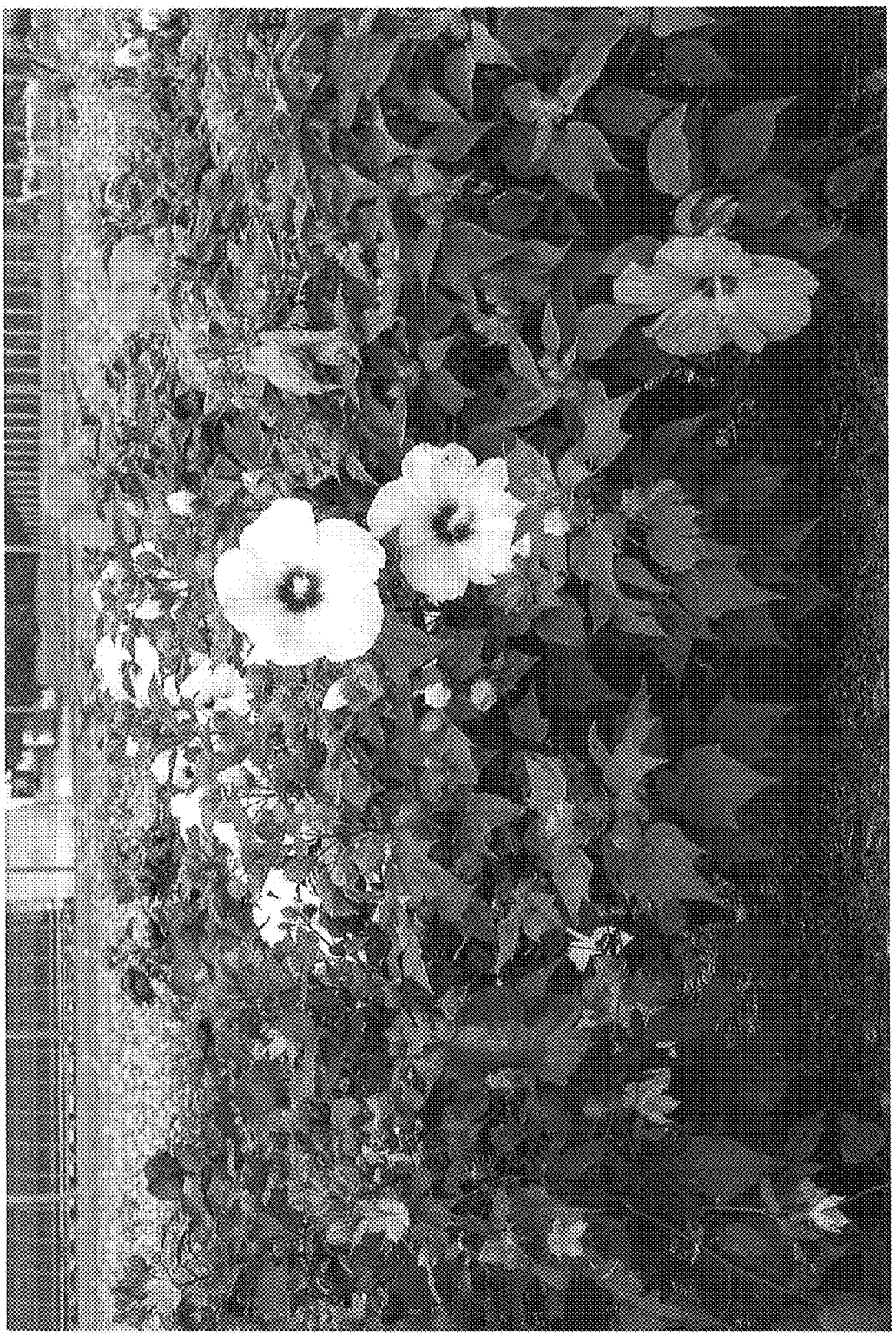
Figure 3:
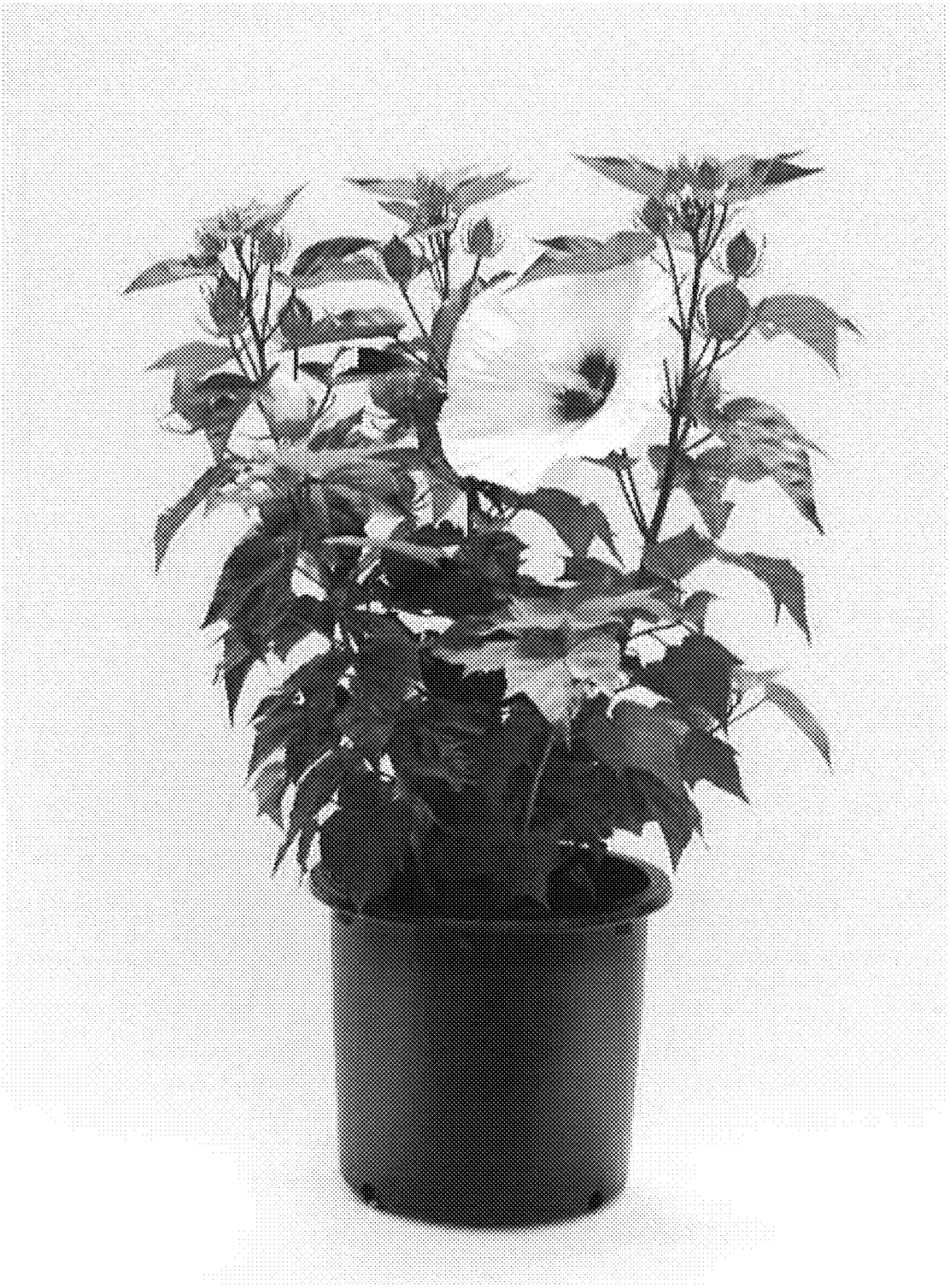
FIG. 3 is a photograph of a typical 2-year-old *Hibiscus* 'RutHib5' potted plant showing its form and flowers.
Figure 4:
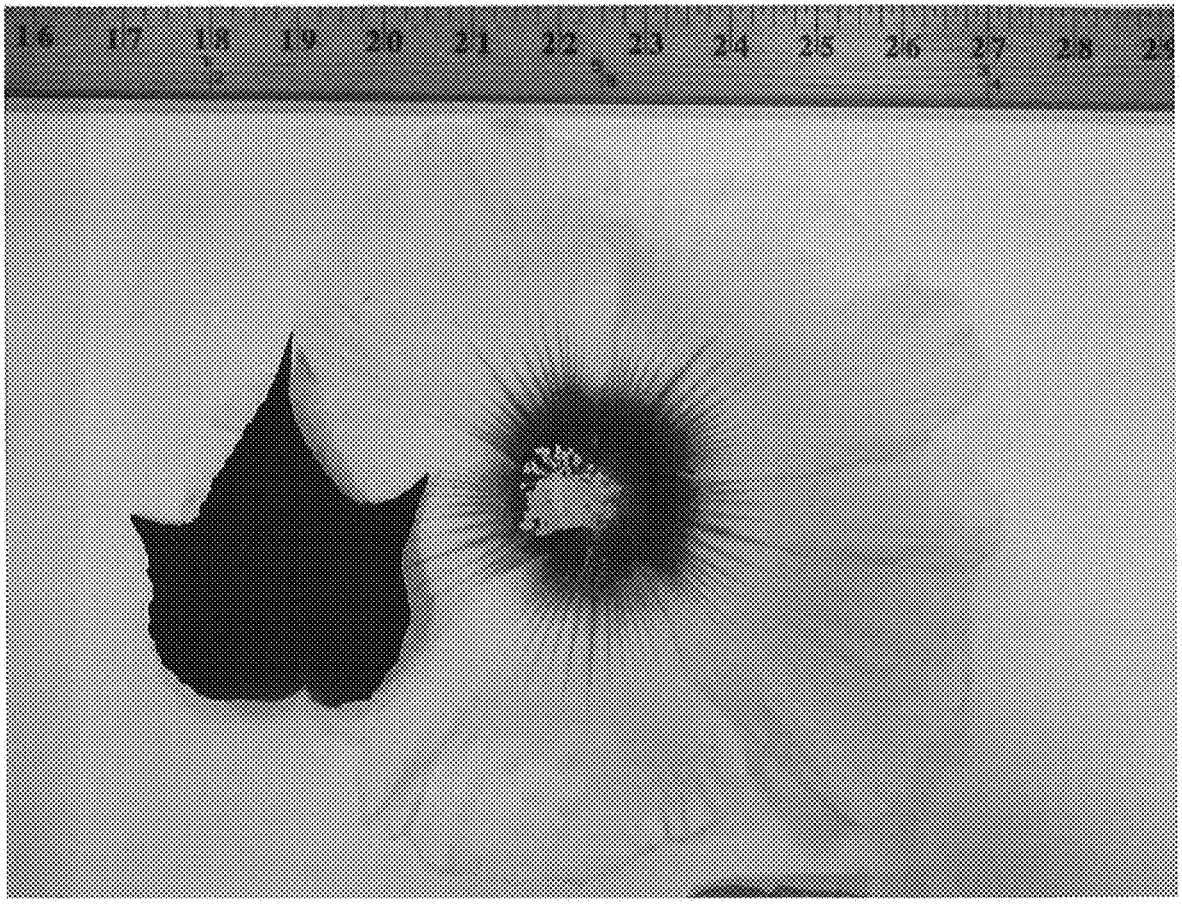
FIG. 4 is a close up photograph of a flower and leaf of the "RutHib5' photograph with a ruler to show the size, shape, and coloring of a typical flower and leaf of the new *Hibiscus*.

The following traits have been consistently observed in the original plant of this new variety and in asexually propagated progeny grown from vegetative cuttings in Watkinsville, Ga., and West Grove, Pa., and, to the best knowledge of the inventors, their combination forms the unique characteristics of the new variety 'RutHib5'.

Throughout this specification, color names beginning with a small letter signify that the name of that color, as used in common speech, is aptly descriptive. Color names beginning with a capital letter designate values based upon The R.H.S. Colour Chart, $6^{th}$ edition published by The Royal Horticultural Society, London, England in 2015, except where general terms of ordinary dictionary significance are used.

The aforementioned photographs and following observations, measurements, and values describe plants of the *Hibiscus* cultivar named 'RutHib5'. Data were collected from 2-year old field plants grown outdoors and planted in the ground on a horticulture farm and nursery in West Grove, Pa. with no trims. The average low temperatures ranged from about 0° F. to 5° F. in the winter and about 48° F. to 84° F. in summer. The data below were collected in the month of August of 2020.

Botanical classification: *Hibiscus* 'RutHib5'.

Commercial classification: Ornamental shrub.

Parentage: [*Hibiscus moscheutos* 'RutHib2' (U.S. Plant Pat. No. 30,853) x *Hibiscus grandiflorus* (unpatented) =Hib2015-76] x *Hibiscus moscheutos* 'RutHib2'.

Growth and propagation:

*Propagation type.*—Vegetative terminal cutting.

*Growth rate.*—Root initiation two weeks, rooted cuttings in 4-6 weeks if taken before flowering, root-zone temperature of 65-75F.

*Root description.*—Fleshy and dense.

Plant description:

*Form.*—Hardy herbaceous shrub, with white flowers having vivid fuchsia centers, blooms from July to November in Southeastern, Pa. and is in full bloom in June and July in GA.

*Habit.*—Upright, spreading, mounding, with 12 to 15 thick upright and heavily branched main stems producing a upright spreading mound to about 101.6 cm tall and about 121.5 cm wide, widest about 90 cm above soil line; 8 to 10 primary branches per main stem protruding at about 80° from horizontal for lowest branches to about 45° angle from horizontal for distal branches, flowering from base to top of plant with about 40 to 48 flowers per main stem.

*Usage.*—Various uses, such as container patio plants, potted plants, landscape use such as border, hedge, and mass planting.

*Vigor.*—Intermediate.

*Size of plant.*—A. Height: About 101.6 cm. B. Plant diameter and area of spread (diameter of the canopy): About 121.5 cm.

*Stem.*—A. Color (RHS): 1. Main Stem: Base 143D; distal portion: between RHS 183D and RHS 186A. 2. Lateral Branches: Nearest RHS 183D. B. Length: main stem, average about 89.0 cm tall, up to about 100 cm tall; lateral branches, about 31.2 cm. C. Diameter: base, about 18 mm-2.3 cm; lateral branches, about 7.0 mm. D. Pubescence: none; glabrous. E. Shape: Terete. F: Odor (of bruised stem): none. G: Description: glaucous. H: Strength: non-lodging.

*Internode.*—A. Number: about 12 nodes pers stem below flowers, average internode length about 3.5 cm of unpinched plant below flower and average about 2.5 cm in upper flowering section without branches, largest in middle portion of stem. B. Color: between RHS 183D and RHS 186A.

*Leaf.*—A. Mature size (L×W): About 14.0 cm to about 16.0 cm long×about 13.0 cm to about 16.0 cm across, becoming smaller distally. B. Arrangement on stem: alternate. C. Leaf number: single. D. Color (RHS): Adaxial color nearest to 147A with blotches of 183D; abaxial color between 148B and 194A. E. Apex: attenuate Base: rounded. F. Margin: dentate. G. Shape: lobed, lobes are shallow to deeply cleft, depending on the leaf. H. Number of lobes: mostly three-lobed with some five-lobed. I. Pubescence: adaxial — occasional, abaxial — moderate. J. Venation: Palmate; lustrous; ridged on abaxial. K. Vein color: Adaxial proximally nearest RHS 183A; abaxial between RHS 186B and 34D. L. Texture: glabrous, lustrous adaxial center, dull adaxial sides and below. M. Odor when crushed: none detected.

*Petiole.*—A. Length: about 6.5 cm. B. Shape: mostly terete, slightly flattened at base. C. Color (RHS): Adaxial between RHS 176B and RHS 166A; abaxial between RHS 146D and 147C. D. Pubescence: glaucous. E. Diameter: about 4.0 mm. F. Texture: glabrous.

*Inflorescence(s).*—A. Type: axillary, single. B. Number per Plant: about 10 blooms average/plant at one time. C. Size (L×W): about 21 cm×21 cm. D. Color (RHS): RHS 49D with red glossy eyespot RHS 59A. E. Longevity: 1-2 days. F. Peduncle. 1. Length: about 3.0-9.0 cm. 2. Diameter: about 4.0 mm. 3. Color (RHS): upper peduncle 143C; lower peduncle 59A. 4. Surface Texture: smooth. 5. Strength: strong. 6. Aspect: 45 degrees.

*Flower.*—A. Number per Inflorescence: about 3-5 per stem in a cluster with blooms opening one at a time.

B. Axillary or Terminal: axillary. C. Symmetry: radial. D. Size: height, about 7.0 cm; diameter, about 21.0 cm. E. Pubescence/Texture: glabrous. F. Flower form/profile: form is large, whirled, and conspicuous; profile is flat with protruding reproductive parts. G. Color at peak bloom (RHS): 1. Upper surface: 49D with 59A glossy eye. 2. Lower surface: 49D. H. Fragrance: none detected. I. Duration: approximately 2 days on the plant. J. Time range for showiness: blooms from July to November in Southeastern, Pa. K. Bud: 1. Color (RHS): 185A when opening. 2. Shape: ovoid. 3. Length: about 5.5 cm. 4. Width: about 3.3 cm. L. Petals: 1. Number: 5. 2. Shape: Broadly obovate, overlapping on either side, palmately veined. 3. Size (l×w): about 10.5 cm×about 11.0 cm. 4. Apex: rounded. 5. Base: cuneate. 6. Margin: entire. 7. Color at when first and fully opened (RHS): i. Upper surface: 49D with 59A glossy eye. ii. Under surface: 49D. 8. Petal drop: Average. 9. Texture: smooth. 10. Arrangement: radial, actinomorphic. 11. Eye zone: present, about 2 cm in length, medium compared to other varieties. 12. Eye zone extensions: present, about 8 cm long, long compared to other varieties. M. Epicalyx: 1. Margin: entire. 2. Texture: glabrous, dull surface abaxial and adaxial. 3. Shape: linear with sharply acute apex and attenuate base, arcuate upwards near calyx. 4. Number: 10-12 per flower. 5. Size: about 3.2 cm long tapering to base of about 3.0 mm wide. 6. Color: adaxial and abaxial color between RHS 144A and 143C with abaxial tinting of nearest RHS 183C. N. Sepal(s): 1. Number: 5. 2. Size (l×w): about 4.0 cm×about 2.5 cm. 3. Shape: deltoid. 4. Apex: acute to aristate. 5. Base: fused to a cup shape in about 1.5 cm. 6. Margin: entire. 7. Texture: under surface puberulent. 8. Pubescence: moderately stellate. 9. Color at peak of bloom (RHS): a. Upper surface: 145A. b. Lower surfaces: 144B. O. Male reproductive structures (stamens): 1. Number: Approximately 180. 2. Staminal column length: about 5.0-7.0 cm. 3. Anther: a. Size: about 1.0 mm long. b. Shape: oval. c. Color (RHS): 162D. d. Number: About 180. e. Texture/pubescence: fleshy, crystalline. 4. Filament: a. length: about 5.0 mm. b. Color (RHS): 158C. c. Texture: clear, occasional minute hair. 5. Pollen: a. Quantity: numerous. b. Pollen color (RHS): 158A. P. Female Reproductive structures: 1. Pistil: a. Shape: rounded. b. Size: length, about 5.0 cm; width, about 5.0 mm. c. Position (superior, inferior, etc.):superior. d. Color (RHS): column 61C to 60B at the end tip. e. Pubescence: few short hairs, bulbous at base. f. Arrangement: split in distal about 7.0 mm portion into 5 branches from column. g. Branch diameter: about 1.5 mm. 2. Stigma: a. Shape: round. b. Color (RHS): 160C. c. Diameter: about 3.0 mm. d. Pubescence: none. 3. Style: a. Length: about 1.8 cm. b. Shape: round. c. Color (RHS): 158D. d. Pubescence: few short hairs, bulbous at base. 4. Ovary: a. Shape: conical. b. Color (RHS):187B. c. Pubescence: none.

*Fruit.*—A. Type: Loculicidal capsule; puberulent; globose, with abruptly acute apex. B. Size: about 10.0 mm diameter. C. Depth: about 1.0 cm. D. Shape: Start/Urn shaped. E. Color: 154C. F. Surface texture: smooth.

*Seed.*—A. Description: Minutely floccose, typically globose. B. Size: about 4.0 mm in diameter. C. Color (RHS): between 158B and 158C. D. Count: about 46.

Weather/temperature tolerance: Plants of the new *Hibiscus* have been observed to tolerate temperatures from about −5° F. to about 100° F. and have been observed to be very tolerant to full sun, wet soils, mild drought, loam to clay soils conditions.

Disease/pest resistance: Plants of the new *Hibiscus* have been observed to be resistant to plants and pests common to *Hibiscus*, such as but not limited to Alternaria alternata, Cercospora, and aerial phytopthora. It also exhibits good to moderate resistance to *Hibiscus* sawfly (*Atomacera decepta*) and intermediate resistance to bacterial leaf spot (*Pseudomonas* and *Xanthomonas*).

It is claimed:

1. A new and distinct cultivar of the *Hibiscus* plant named 'RutHib5' as illustrated and described herein.

* * * * *